United States Patent [19]

von Blücher

[11] Patent Number: 4,677,019
[45] Date of Patent: Jun. 30, 1987

[54] CARBON-CONTAINING PROTECTIVE FABRICS

[76] Inventor: Hubert von Blücher, Freytagstrasse 45, D-4000 Düsseldorf, Fed. Rep. of Germany

[21] Appl. No.: 731,421

[22] Filed: May 7, 1985

[30] Foreign Application Priority Data

Dec. 1, 1984 [DE] Fed. Rep. of Germany ....... 3443900

[51] Int. Cl.⁴ .............................................. A61L 15/00
[52] U.S. Cl. .................................. 428/244; 428/283; 428/323; 428/408
[58] Field of Search ................ 428/244, 283, 408, 323

[56] References Cited

U.S. PATENT DOCUMENTS 4,454,191  6/1984  von Blücher et al. .............. 428/244
4,455,187  6/1984  von Blücher et al. .............. 428/244
4,510,193  4/1985  von Blücher et al. .............. 428/244

Primary Examiner—Marion C. McCamish
Attorney, Agent, or Firm—Sprung, Horn, Kramer & Woods

[57] ABSTRACT

A material for protection against chemical pollutants is produced by spraying onto a base fabric a mixture of activated carbon and a polymer binder to produce an open-pored foam structure which does not materially reduce the air permeability. The binder is permeable to the pollutant so the latter can reach the carbon, and the binder is less than 20% of the coating.

11 Claims, 5 Drawing Figures

CARBON-CONTAINING PROTECTIVE FABRICS

The use of adsorbents is recommended whenever specific substances are intended to be eliminated from a mixture. Activated carbon (A-carbon) holds a singular position among the adsorbents which is ascribed to the high adsorptive capacity, entailed by a very large inner surface and the relatively non-specific adsorptive capacity, i.e. to a physical adsorption. Moreover, by selecting the appropriate initial material and the kind of activation, activated carbon may be adapted to the respective range of application.

An important application of activated carbon are the flexible flat-shaped filters which are used for industrial purposes, in households and also for protective clothing. They usually consist of a carrier, which is frequently a textile fabric onto which a mixture of a binder and adsorbent is applied by dip coating and squeezing off. The binder results in a reduced adsorptive capacity and always leads to an undesirable change of the feel characteristics of the textile fabric because the filaments will stick together, which is a handicap especially in the case of clothing (protective clothing).

An essential improvement was achieved with the protective material of DE-PS No. 29 51 827 which consists of an air-permeable flexible carrier layer carrying on one or both sides grains of an adsorbent, having a diameter of about 0.5 mm, on support columns comprising a solidified adhesive composition. These permeable flat-shaped articles meet many requirements, however, their manufacture is complicated and, in view of the necessary granular adsorbent, for example, fine grained activated carbon, are relatively expensive.

The same disadvantage of complicated, and therefore expensive, manufacture applies to the flat-shaped filters according to German Offenlegungsschrifts No. 32 11 322 and No. 33 04 349. In the first case, a mixture of a pulverulent adsorbent and a polymer binder is imprinted in a specific pattern on an air-permeable flexible carrier layer. In the second case, the adhesive material is first imprinted in a specific pattern or merely coated on the prominent sections of a tissue and activated carbon granules are subsequently fixed thereon. The use of granules of activated carbon having a grain size of from about 0.2 to 0.4 mm guarantees a good adsorptive capacity and a favorable adsorption kinetics, however, its manufacture necessitates additional and partly complicated process steps. The abrasive resistance of the protective materials according to DE-PS No. 29 51 827 and DE-OS No. 33 04 349 does not meet the requirements of practice. A common feature of the prior art flexible flat-shaped filters is that, as a result of the processing, the proportion of adhesive or bonding agent, based on the activated carbon, is relatively high.

Therefore, the object of the invention is to optimize the basical properties of a protective material against volatile substances, in particular war gas, and to simplify its manufacture.

It is important, in particular when the protective material is designed to be used for clothing, that the air permeability of the textile fabric used as carrier layer is only minorily reduced by the application of activated carbon and that the textile feel of the ground texture is substantially maintained. To this end, the activated carbon must be fixed with as little binder as possible. Nevertheless, the coating should be very abrasive resistant and contain a maximum amount of activated carbon per unit area.

Further problems that are solved by the invention will become apparent from the advantages described in connection with specific embodiments.

This requirement is met by the method according to the invention, comprising spraying the finally tacky granules or droplets of bonded activated carbon on the flexible carrier material. The method of the subject invention utilizes directly commercial pulverulent activated carbon having a particle size of from 0.1 to 50 $\mu$m, preferably from 1 to 10 $\mu$m. For example, an activatived carbon ground with jet mills may be used in which 95% of the particles are smaller than 3 $\mu$m. The inner surface of the activated carbon, determined according to the BET method, amounts to from 600 to 1500 square meters per gram. Since the invention succeeds in accommodating unusually large amounts of activated carbon in the coating and, in particular in a composite material, it is also not necessary to use high-quality types of activated carbon.

If it is desired to manufacture according to another substantial aspect of the invention a self-decontaminating protective material, enzymes and/or immobilized cells are incorporated in the meso- and/or micropores of the activated carbon, said enzymes or cells being capable of decontaminating chemical polluants, in particular war gas. The cells or enzymes are in particular of the type that can decompose phosphoric acid esters.

Cell cultures of the kind are, for example, PARATHION splitting Pseudomonas isolates. The immobilization of living cells takes place by bonding to the activated carbon as carrier. After having prepared in a manner known per se a mixed culture by fermentation, which contains, for example, from 3 to 4 g cells per liter, one allows about 30 volume percent thereof to be adsorbed by the dry activated carbon and obtains a, now as before, dry activated carbon which is, however, heavy in view of the absorbed water, which contains then about 1 g of the cells per liter, in the absorbed form. An activated carbon powder of the kind, which is self-decontaminating, may be directly used for the purposes of the invention because the usually desired sheathing or encapsulation may be brought about by the polymer binder upon spray coating.

The sheathing of the activated carbon particles, in particular those which already contain absorbed immobilized cells and/or enzymes, takes place by covering with a thin layer of polymers having a selective permeability for the substances to be adsorbed.

The thickness of the encapsulating layers may be in the range of the diameter of the macromolecules up to the micrometer range. For example, it is possible to surround activated carbon particles with a film of macromolecules by pretreating the particles with acrylate dispersions, e.g. Acronal 50 D and 27 D of BASF, said film being permeable to the desired adsorbates, in particular chemical polluants or war gas, but not for sweat, detergents, oils and fats. The latter is important when protective materials are used for protective clothing of composite structure in order to prevent an inactivation as a result of wearing the clothing for a long period of time under the utmost physical strain and to ensure a high prolonged protection against chemical polluants.

Encapsulated activated carbon particles may be used for the purposes of the invention whenever a self-decontamination is not necessary, the manufacture of carbon particles of the kind is described, for example, in DE-OS No. 33 04 399.

In addition to the activated carbon, also other known adsorbing materials may be used for the coating, such as silicic acid, xerogels, metal oxides and hydroxides, in particular aluminium oxide and hydroxide, molecular sieves, ion-exchangers in the form of powders of about the same size as the utilized activated carbon.

According to a preferred embodiment of the invention, flame proofing agents are used therewith which additionally make the protective material difficult to inflame. Preferred flame proofing agents are those comprising mainly antimony trioxide in combination with bromine compounds. These function as radical scavengers in the gas phase and, therefore, act at a certain distance. The flame proofing agents are preferably admixed to the polymer binder.

Various kinds of polymer binders may be used for the purposes of the invention, for example, polyurethanes, polyacrylates, e.g. ACRONAL, or elastomers. The latter also in the halogenated form, in particular chlorinated or fluorinated, such as NEOPREN or BAYPREN. The binders are preferably utilized as aqueous dispersions. Furthermore, solvent-free polyurethane systems may be used, such as those marketed under the name "High Solids" (BAYER). Very suitable are also fusion adhesives consisting mainly of polyamides, polyesters, or ethylene-vinylacetate-copolymers. The binder should be of high molecular weight or pre-cross-linked to the extent that it does not penetrate into the mesopores of the activated carbon. In most cases, in particular when the activated carbon has been admixed to the binder prior to the spraying, the polymer binder will perform the double function of the above-discussed sheathing of the A-carbon particles and their adhesion to each other and to the carrier layer.

If, according to the preferred embodiment of the invention, the binder is uilized as liquid, mostly viscous system, i.e. as solution or dispersion, and the A-carbon is admixed prior to spraying, this pulp will be sprayed on through a nozzle in the direction of the carrier layer. This takes place in a manner known per se, without any nebulized air, with so-called AIRLESS sraying devices wherein a special pump supplies the pressure of up to 300 bars, usually of about 250 bars, necessary for spraying. Spraying without nebulized air is useful in the process of the invention not only because the sprayed material does not rebound from the carrier layer, but because the transport of the material from the nozzle to the carrier layer takes place without any gas stream, especially because according to the invention, the spray is in most cases subjected to the action of hot gases. These are passed, in particular in a tunnel, in the direction of spraying and are preferably produced by adapting the tunnel to be a combustion chamber. There are provided in the casing of the tunnel-like combustion chamber, in its bottom part, gas burners, similar to propane burners or blow torches, which are inclined towards the spraying direction.

It is also possible to spray with nebulized air, however, in that case more air would have to be heated and the dust nuisance in the ambient air would be by far greater and requires special arrangements. The intention of keeping the environmental load as low as possible is also the reason for preferring the aqueous binder dispersions or systems because in that case solvent vapors will not be produced which would have to be sucked off and adsorbed. Moreover, when using inflammable solvents which already escape as vapor from the spray before the latter comes into contact with the hot gases in the combustion chamber, there is the danger of undesirable deflagrations.

The rapid evaporation of the water, used as preferred carrier medium, after the spraying can be promoted by preheating the material to be sprayed on. The selection of the suitable temperatures depends on whether the mixture to be sprayed on, in particular the activated carbon suspended therein, contains heat-sensitive substances, such as immobilized cells. In this case, the preheating temperature and the temperature attainable in the droplets of the spray would have to be adapted thereto. Otherwise, a preheating to temperatures of up to 300° C. is possible and desirable in order to make the spraying easier.

It was found that the spraying of the mixtures of activated carbon, binder and water, in particular if they have the consistency of a thick pulp or paste—inspite of the delivery to the nozzles at a pressure of up to 300 bar—is possible only if the spraying nozzle is excited in a manner known per se by ultrasonic oscillating means, so-called sonotrodes, to sonic frequencies of from 20 to 60 kHz. Due to the ultrasonic oscillation, the conveyed pulp at the spraying nozzle is disrupted and is converted to the fine spray, the droplets of which progressively loose their water, or their carrier liquid, in flight to form droplets or adhesive spherules of activated carbon and heated or molten polymers which adhere to the carrier layer as soon as they impinge thereupon and solidify upon cooling.

The process may be conducted substantially continuously by unwinding a continuous web of the material of the carrier layer—in particular a non-woven fabric or tissue conventionally used for protective clothing—from a supply roll and spraying the same repeatedly and successively in one step in the manner described above until the desired coating thickness is obtained. The spraying nozzles are serviceably arranged directly in advance of the tunnel for feeding the hot gases and the mentioned combustion chambers, which usually have a length of from 30 to 50 centimeters. There usually remains a free space of from 80 to 100 centimeters between the tunnel and the carrier layer. Thus, the nozzles are arranged at a distance of from about 1 to about 1.80 meters from the web of material onto which the activated carbon-binder-mixture is to be applied. It is useful to conduct the spraying as broad jet transversally to the direction of advance of the carrier layer.

When the operation is carried out accordingly, the sprayed on very fine droplets adhere to the surfaces of the threads of the tissue facing the nozzle and also partially penetrate into the tissue. At first, the coating has the appearance of fine "fly-speck" with free spaces of tissue remaining inbetween. After one or several further spray coatings in the same step, the coating spots become larger, however, they grow together bridge-like so that the penetration of air through the tissue is hardly impaired. The magnification shows an open-pored foam structure and under the microscope a structure resembling coral trees or skeletons.

Depending on the size of the anchored small heaps of bonded activated carbon on the carrier layer of, for example, between 0.5 and 0.1 mm, from 4 to 100 millions of said heaps can be accommodated per square meter. Since the doplets or spherules grow together and adhere to each other as soon as they impinge on the surface and are seldom larger than 0.3 mm, there are usually between 10 and 60 millions coating spots per square meter of carrier surface. The height of the coating layer is achieved less by a single spraying operation than by repeated spraying in one pass of the moving web. This can easily take place up to 10 times.

Thus, the coating of activated carbon anchored on the carrier may attain a height of up to 1 mm.

The invention will be further described with reference to the accompanying drawings, wherein.

Figure 1:
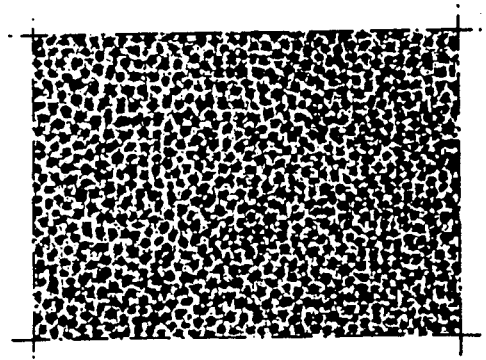
FIG. 1 is a plan view in about four-fold magnification of a tissue partially coated with bonded activated carbon in accordance with the invention.

The described process may be varied in different ways without abandoning the scope of the invention. For example, it is possible to spray a solution or dispersion of the polymer binder at first alone under pressure, again preferably without supplying nebulized air, in the direction of the carrier layer and to blast the activated carbon powder into the spray. The powder and the droplets unite thereupon in flight and are again subjected to the action of hot gases to form tacky spherules or droplets of bonded carbon while the solvent or dispersing agent is converted into vapor, said spherules or droplets adhere to the carrier layer as soon as they impinge thereupon and solidify upon cooling.

Since this embodiment teaches to spray a viscous solution or dispersion, but no thick pulp or a paste, it is not absolutely necessary to let the spraying nozzle oscillate at ultrasonic frequency to form droplets of desired size. The excitement of the nozzle by means of sonotrodes is also possible in this case and may even be advantageous, depending on the composition of the binder system and the additives which are already admixed thereto.

Instead of a solution or a dispersion of the polymer binder, also molten binders, such as fusion adhesives or the mentioned "High Solids" may be sprayed, into the spray of which again activated carbon powder may be blasted.

The latter is then substantially bonded by the fine droplets of the spray and at the latest when they impinge upon the carrier layer, tacky spherules of bonded activated carbon are formed which adhere to the carrier layer and solidify upon cooling. It may also be advantageous in this case to subject the spray together with the activated carbon, which is at least partially absorbed thereby, to the action of hot gases.

Finally, the process of applying bonded activated carbon on a carrier layer, taught by the invention, may be varied to the effect that both pulverulent activated carbon as well as a pulverulent fusible polymer binder are blasted in the direction of the carrier layer. However, it is necessary thereby to subject these dusts in flight, again advantageously in a tunnel or a combustion chamber, to the action of so hot gases that the binder melts and the binder droplets unite with the activated carbon particles, at the latest when they impinge upon the carrier layer with the activated carbon particles. A carrier gas, which may also be preheated, is necessary thereby for the transport of the activated carbon powder and the fusible binder, however, the bounce of the impinging particles which partly occurs thereby, as well as during the spraying with compressed air, is particularly negligible when the carrier material exhibits a high air permeability. Particularly suited for this mode of operation are the above-mentioned fusion adhesives or "High Solids" which are sold as powders.

The composition of the air-permeable coating on the carrier layer, in particular a textile fabric, depends on the desired additives to the activated carbon and the binder. Accordingly, the coating of bonded activated carbon may also contain other adsorbates or flame proofing agents. The ratio of binders to activated carbon is adjusted such as to ensure the necessary adhesion of the coating on the carrier layer and a sufficient bonding within the activated carbon coating and, accordingly, a minor abrasion. Surprisingly enough, the process of the subject invention can do with from 5 to 15 parts of binder per 100 parts of activated carbon. On the whole, a flexible air-permeable protective material is produced which contains in the partial coating of bonded activated carbon from 50 to 250, preferably from 80 to 220 grams of activated carbon per square meter.

Figure 2:
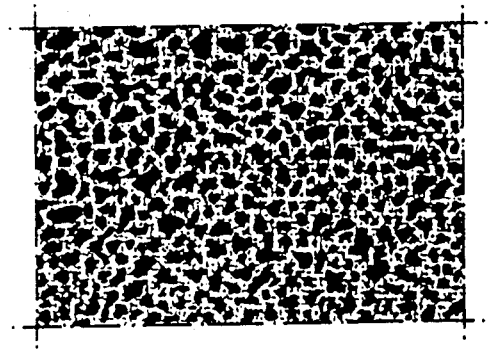
FIG. 2 is a plan view in about four-fold magnification of a tissue similar to FIG. 1 but which has been sprayed with a levelling agent in addition to carbon-binder.
Figure 3:
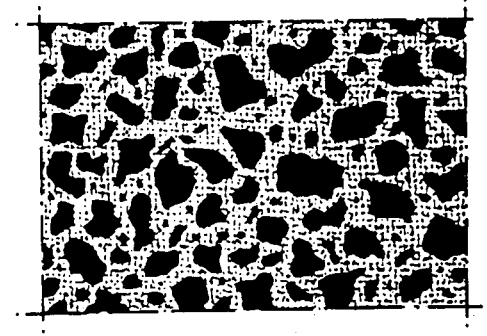
FIG. 3 is a view similar to FIG. 2 except that more levelling agent was employed.

The kind and thickness of the bonded activated carbon coating may be varied not only by varying the mode of operation, the conditions during spraying and repeated spraying in one step, but can also be lastingly varied by spraying into the spray of activated carbon-binder-mixture a release or levelling agent. These substances which increase the surface tension are inter alia familiar in connection with the water-repellent finish of textiles. From a chemical point of view, these are, for example, polyvinylidene fluoride-hexafluoropropylene-copolymers, silicons, such as silicon 230 (WACKER) or the known impregnating agent SCOTCH GUARD (3M-COMP.). These release or levelling agents are suitably sprayed as dispersion in a carrier directly behind the spraying nozzle in the main stream, for example, at an angle of 45° and passed through the combustion chamber together with the spray. Due to the amount of this additive, which can be provided in one pass of the textile web, but only in the case of some of the tandem joined nozzles, the coating spots of the bonded activated carbon coalesce to form "islands" which can have the size of some millimeters, between which equally large free spaces of carrier tissue remain, so that almost nothing is covered. FIGS. 1, 2 and 3 show in fourfold magnification how the partial coating may be varied by the progressive addition of the release or levelling agent during the spraying operation. A textile protective material such as illustrated in FIG. 3 is particularly suitable for protective clothing in the tropics because here the air and water vapor penetration in outward direction is particularly high. Although the activated carbon coating in these "islands" attains a diameter of a few millimeters, the air-permeability of the carrier layer is reduced by at most 20%, usually only by less than 10%, surprisingly enough also in this embodiment.

Apparently due to the already mentioned "coral structure", also the feel chracteristics of a textile protective material of the kind remains excellent. Even in the case of a very thin textile fabric with particularly high air permeability as carrier material, for example, a thin plastic nonwoven fabric, the surface turned away from the spraying nozzle fully maintains its original textile appearance and does not change dyes applied thereon which are adapted for the infrared reflection. Thus, the activated carbon coating penetrates into the textile fabric, which is advantageous for the anchoring, however, it does not penetrate therethrough.

Finally, the structure of the bonded activated carbon coating may be modified by spraying on conventional rapid cross-linking agents, so-called stoppers, to the effect that the droplets of the spray are already substantially solidified when they are applied and are only adhesive inasmuch as it is necessary for their adherence on the carrier layer or the already present coating. The procedure is here analogous to that described in the case of the release and levelling agents and it is also possible to influence the structure of the bonded activated carbon coating by the selection of the spraying procedure in which the rapid cross-linking agent is co-applied. It is possible, for example, in six successive spraying steps on the same textile web, when using the same binder, to add in the second and third step a stopper and only in the last step a release agent. Being familiar with the invention, variants of the kind can be performed by those skilled in the art and the result can be readily examined by a comparison with the above-mentioned essential characteristics of protective materials, such as the amount of activated carbon per surface unit, abrasion resistance and textile feel. The skilled artisan can modify, as described above, the partial coating of bonded activated carbon anchored on the carrier layer to obtain a height of from 0.05 to about 1 mm and a diameter of from 0.1 to 5, preferably from 0.2 to 1 mm.

The process of the subject invention was hereintofore described substantially in connection with the application on textile fabrics as carrier layer, such as used for protective clothing. However, it is, of course, possible to use it for the manufacture of other protective and sheathing materials against chemical or biological noxious matter, other carrier materials, e.g. screen cloth, perforated films etc..

Since the necessary spraying device comprising the nozzle, which preferably oscillates at ultrasonic frequency, and the combustion chamber following thereupon is relatively small and handy, the process of the subject invention offers the possibility of providing already available protective clothing, for example, protective suits, in this manner with a self-decontaminating protection against chemical pollutants. Whether the coating taught by the invention should be applied on the inner or outer surface, depends on the intended use.

In as much as it proves to be necessary—in view of the chemical nature of the binder, the selected method of application, for example, as aqueous dispersion—to dry the carrier layer with the partially applied bonded activated carbon, this may be done at moderate temperature, in that the webs provided with the coating are further passed through a heated drying section. Inasmuch as the activated carbon contains enzymes or immobilized cells, the temperature should not exceed 40° C., unless the web of material is moved at such a speed that the elevated temperature is not detrimental due to the short reaction time of the biocatalysts. To this end, the drying may be improved, if necessary, by the application of vacuum.

Finally, the carrier layer in the described continuous coating on a moving web with the partially coated bonded activated carbon may be stored on tightly wound rolls under winding pressure for a few days at 30° to 40° C.

Figure 4:
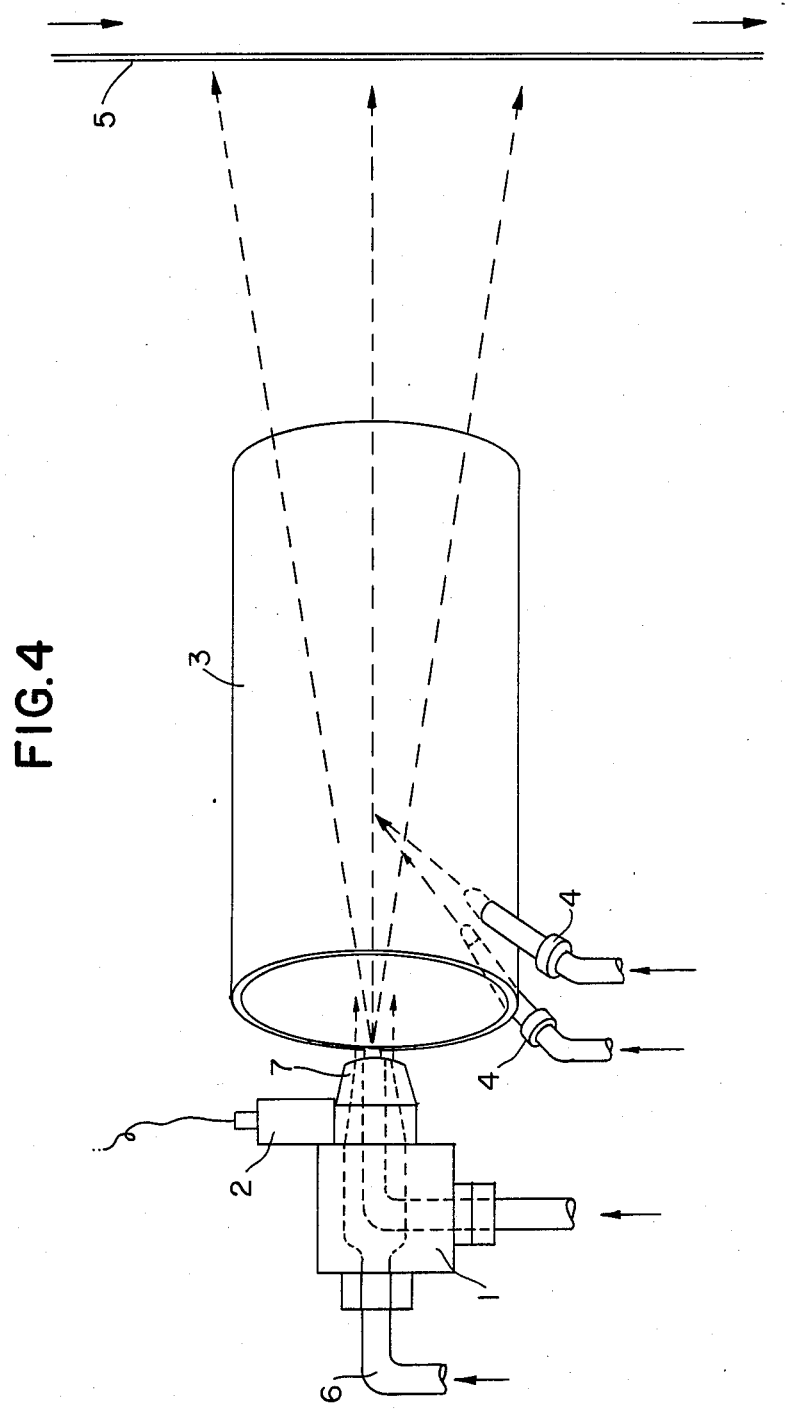
FIG. 4 is a schematic perspective view of a spraying apparatus for coating the instant fabrics.

FIG. 4 shows a coating device comprising airless spray pistol 1, an ultrasonic oscillating means 2 provided at the nozzle, combustion chamber 3 with burners and the carrier layer 5, scaled down and diagramatically represented, arranged at a distance from the combustion chamber. A release agent or a rapid cross-linking agent can be passed via conduit 6 to annular nozzle 7 arranged about spraying nozzle 1.

Figure 5:
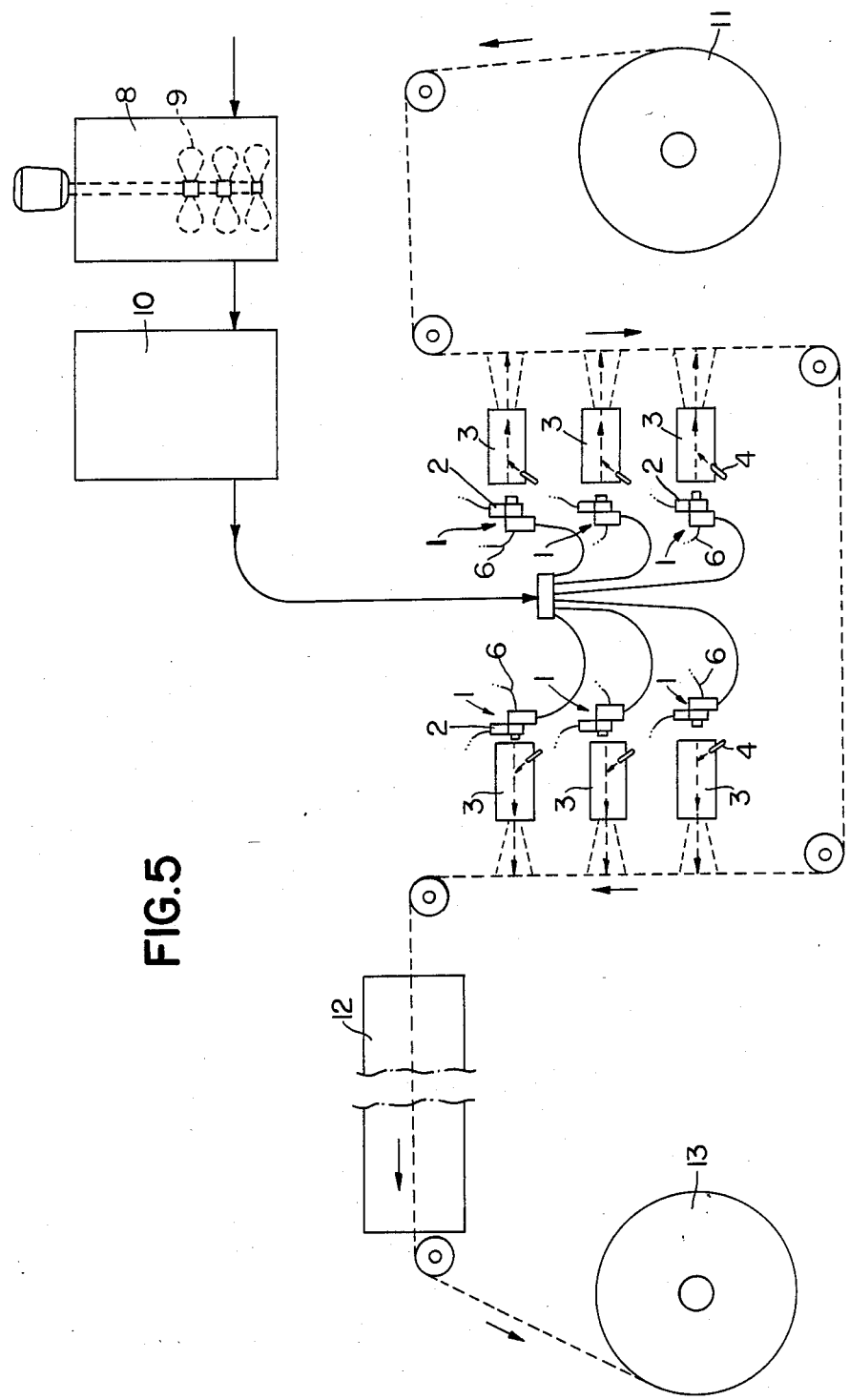
FIG. 5 is a schematic illustration of an overall system for producing the instant coated fabrics.

The process of the subject invention will be described in the following by way of example, relying on FIG. 5:

A specific cell culture produced in a manner known per se by fermentation containing about 3% cells in water, if mixed in container 8, which is provided with a "siren mixer" 9, with the threefold volume of activated carbon (95% <30 μm). The activated carbon which is thusly loaded with the cell culture solution is still a dry product. This is then added to 30 parts of a 50% dispersion of a commercial acrylate (Acronal) and to 5 parts by weight of a combined flame proofing agent. The pulp obtained thereby is fed from an autoclave 10 under a pressure of 285 bars to spraying nozzles 1 which oscillate with sonotrodes 2 at an ultrasonic frequency of 50 Hz. After the mixture, which is sprayed without nebulized air, has left the nozzles, it is passed through the tunnel-like combustion chambers 3 which are heated by gas burners 4. The particles of the material of the spray are dried in flight and are blasted in the adhesive condition on the textile web 5 which is unwound from a supply roll 11 and passed past six broad jet nozzles 1 which are provided with burners. After applying the adsorbing bioactive material onto the moving web of tissue, the latter is advanced through a drying section 12 heated to about 60° C. For vulcanization and condensation of the binder in the coating of bonded self-decontaminating activated carbon, the web is stored on tightly wound rolls 13 of about 600 meters under winding pressure for three days. An ambient temperature of from 30° to 40° C. is observed thereby. A laminate comprising a cotton and a mineral fiber web having a total basis weight of about 220 g/m$^2$ was provided with a coating of 150 g activated carbon per square meter. The proportion of binder was 15%. The air-permeability of this laminate amounted, without the coating, to 1500 l/m$^2$ sec and with the partial activated carbon coating 1320 l/m$^2$ sec, in each case at a pressure of 10 mm water column, which corresponds to a reduction of the air-permeability by 12%. This material can be directly used as monopack.

In the same manner, a coating of 80 g activated carbon/m$^2$ was produced on a polyester nonwoven fabric having a basis weight of about 70 g/m$^2$. These two materials were then processed, with the surfaces of their coatings of bonded self-decontaminating activated carbon, to form a bipack material having a total weight of 520 g/m$^2$ which has a completely textile appearance, but contains 200 g activated carbon/m$^2$.

I claim:

1. In a protective material against volatile chemical pollutants, comprising an air permeable flexible carrier layer onto which activated carbon is partially anchored, in uniform distribution, by means of a polymer binder, the improvement comprising utilizing activated carbon particles which have a particle size of from 0.1 to 50 μm and are sheathed with a polymer binder that is permeable to chemical pollutants, said binder protecting the activated carbon against undesirable adsorbates, and spraying the activated carbon-binder mixture onto the carrier layer; the coating having a binder component of below 20% by weight, an open-pored structure and reducing the air permeability of the carrier layer by not more than 20%.

2. A protective material according to claim 1, wherein the flexible carrier layer is a textile fabric.

3. A protective material according to claim 1, including enzymes adsorbed in the meso- and micropores of the activated carbon.

4. A protective material according to claim 3, including immobilized cells which produce said enzymes adsorbed in the pores.

5. A protective material according to claim 4, wherein the enzymes and/or cells are such as decontaminate phosphoric acid esters.

6. A protective material according to claim 1, wherein the coating of bonded activated carbon anchored on the carrier layer exhibits a height of from 0.05 to 1 mm and a diameter of from 0.1 to 5.

7. A protective coating according to claim 1, wherein the binder component in the coating of bonded activated carbon is from 5 to 15 weight percent, based on the activated carbon.

8. A protective material according to claim 1, carrying from 50 to 250 grams of activated carbon per square meter.

9. A protective material according to claim 1, wherein the coating of bonded activated carbon includes a flame proofing agent.

10. A protective material according to claim 1, wherein the coating of bonded activated carbon includes a release agent, levelling agent or impregnating agent.

11. A protective material according to claim 1, each square meter having from 4 to 100 million points of bonded activated carbon having a diameter of from 0.5 to 0.1 mm.

* * * * *